(12) United States Patent
Brand et al.

(10) Patent No.: US 7,958,774 B2
(45) Date of Patent: Jun. 14, 2011

(54) DEVICE AND METHOD FOR SAMPLE PREPARATION

(75) Inventors: Uwe Brand, Fichtenwalde (DE); Falk-Thilo Ferse, Berlin (DE)

(73) Assignee: Waters Technologies Corporation, Milford, MA (US)

( * ) Notice: Subject to any disclaimer, the term of this patent is extended or adjusted under 35 U.S.C. 154(b) by 578 days.

(21) Appl. No.: 11/915,783

(22) PCT Filed: Jun. 2, 2006

(86) PCT No.: PCT/EP2006/005283
§ 371 (c)(1),
(2), (4) Date: Jun. 11, 2008

(87) PCT Pub. No.: WO2006/128717
PCT Pub. Date: Dec. 7, 2006

(65) Prior Publication Data
US 2008/0236256 A1    Oct. 2, 2008

(30) Foreign Application Priority Data
Jun. 2, 2005    (DE) ................. 10 2005 025 440

(51) Int. Cl.
*G01N 13/00* (2006.01)
(52) U.S. Cl. ....................................... 73/61.55
(58) Field of Classification Search ............... 73/61.55; 422/70
See application file for complete search history.

(56) References Cited

U.S. PATENT DOCUMENTS
6,641,783 B1 * 11/2003 Pidgeon et al. .............. 422/70

FOREIGN PATENT DOCUMENTS
SU             905785 B  *  2/1982
* cited by examiner

*Primary Examiner* — Hezron Williams
*Assistant Examiner* — Tamiko D Bellamy

(57) ABSTRACT

A system and method for sample preparation and/or sample enrichment are provided. The system comprises the following components: a first switch element with a switch element input and at least two mutually exclusive switch element outputs and a second corresponding switch element with at least two mutually exclusive switch element inputs and a switch element output, the first and second switch elements being connected to control means for opening and closing the switch element inputs and switch element outputs; a first distributor element with at least three ports and a second distributor element with at least three ports; as well as a first separation column and a second separation column, the components being in such fluidic communication with each other that by means of different positions of the switch elements it is possible to configure at least two different fluidic paths in the system, wherein said different positions are achievable through the control means. The system allows, for example, the simple performance of the backflush process.

10 Claims, 16 Drawing Sheets

US 7,958,774 B2

DEVICE AND METHOD FOR SAMPLE PREPARATION

FIELD OF THE INVENTION

The present invention relates to a system and method for sample preparation and/or sample enrichment and more particularly to a system and method for sample preparation and/or sample enrichment in chromatographic analysis.

BACKGROUND OF THE INVENTION

In chromatographic practice, it is not all that often the case that the solutions under investigation are solutions of pure substances in pure solvents. The matrix under investigation is frequently extremely complex, and a direct injection of the sample is out of the question. Essentially, in the preparation of samples for chromatographic analysis, use is made of a combination of HPLC columns which either are manipulated offline in the form of disposable cartridges or solid-phase extraction cartridges or which, in the form of normal separation columns, are brought into the eluent flow at the correct time by means of switching valves. In this connection, especially where the said process is automated, there are, however, some problems.

Known arrangements for the enrichment of compounds of dilute solutions—in which, first, the compounds to be separated, i.e. the sample, are enriched at a high flow rate on a so-called trapping column and in which, in a second step, the enriched sample is eluted from the trapping column and separated by the analytical column—have the problem that, during loading of the trapping column, in some cases the flow is flushed to the analytical column. Furthermore, worse chromatographic results are obtained, because there is already separation at the trapping column.

Some of these disadvantages can be avoided with the known backflush process. FIGS. 1a and 1b present an arrangement for performing a backflush process, wherein the arrangement employs a 10-port valve with ports a to j. The component to be separated is retarded at the head of separation column A (see FIG. 1a) and is eluted in the opposite flow direction and separated at separation column B, as presented in FIG. 1b. Using this method, it is possible to minimize the peak widening. Furthermore, it is not necessary in this case to take into consideration the selectivity differences between separation column A and separation column B.

However, also the known arrangement, presented in FIGS. 1a and 1b, for providing a backflush configuration has its disadvantages. For example, the arrangement shown in FIGS. 1a and 1b does not allow the online performance of offline processes, such as loading, washing with 5% methanol, washing with 60% methanol plus 2% ammonia and eluting with 60% methanol plus 2% acetic acid. An online process would, in this case, have to be restricted to loading and eluting. Only with considerable effort and expense would it be possible for such processes to be performed online (it would be necessary either to employ an additional low-pressure switching valve or to replace the isocratic pump with a gradient pump), it being impossible to assess the problems of computer-aided control. To summarize, therefore, it can be said of the known method illustrated in FIGS. 1a and 1b that no additional cleaning steps are possible at the first separation column A, i.e. poor online extracts, and that, furthermore, an additional isocratic pump is required.

Therefore, the object of the present invention is to provide a simpler and better system and method for sample preparation with which, for example, the backflush process can be performed.

SUMMARY OF THE INVENTION

The present invention provides a system for sample preparation and/or sample enrichment, the system comprising the following components: a first switch element with a switch element input and at least two mutually exclusive switch element outputs and a second corresponding switch element with at least two mutually exclusive switch element inputs and a switch element output, the first and second switch elements being connected to control means for opening and closing the switch element inputs and switch element outputs; a first distributor element with at least three ports and a second distributor element with at least three ports; as well as a first separation column and a second separation column, wherein the components are arranged in such fluidic communication with each other that by means of different positions of the switch elements it is possible to configure at least two different fluidic paths in the system, wherein said different positions being achievable through the control means.

Further advantageous embodiments are defined in the subclaims.

SHORT DESCRIPTION OF THE DRAWINGS

FIGS. 1a and 1b show a diagram of a known system in which a 10-port valve is employed, for performance of a backflush process, wherein FIG. 1a presents the loading and enrichment step and FIG. 1b presents the elution and separation step.

FIGS. 2a and 2b show a diagram of a system according to the invention for sample preparation by means of the backflush process as well as two fluidic paths through the system, wherein FIG. 2a presents the loading and enrichment step and FIG. 2b presents the elution and separation step.

DETAILED DESCRIPTION OF PREFERRED EMBODIMENTS

Figure 1A:
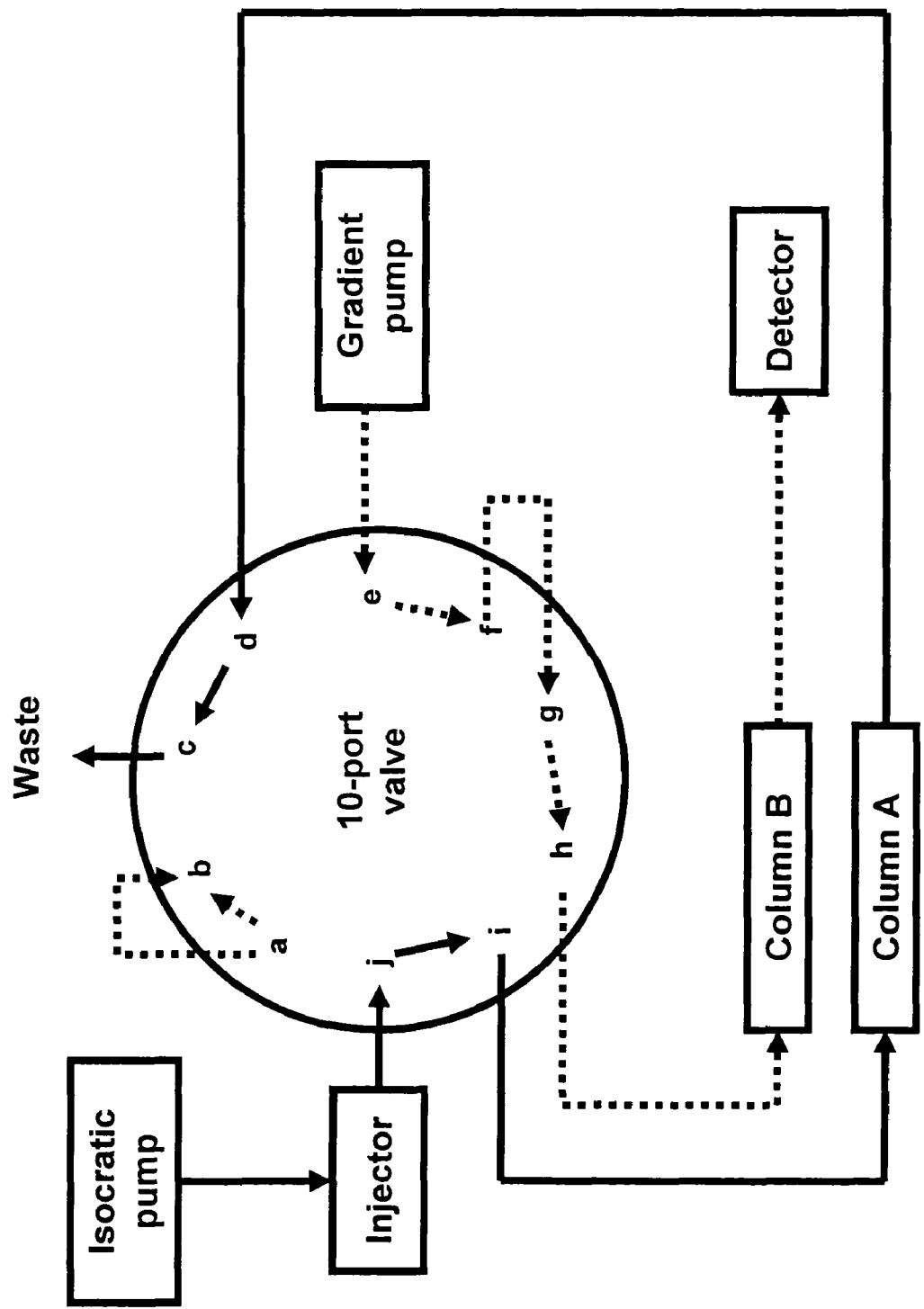
Figure 1B:
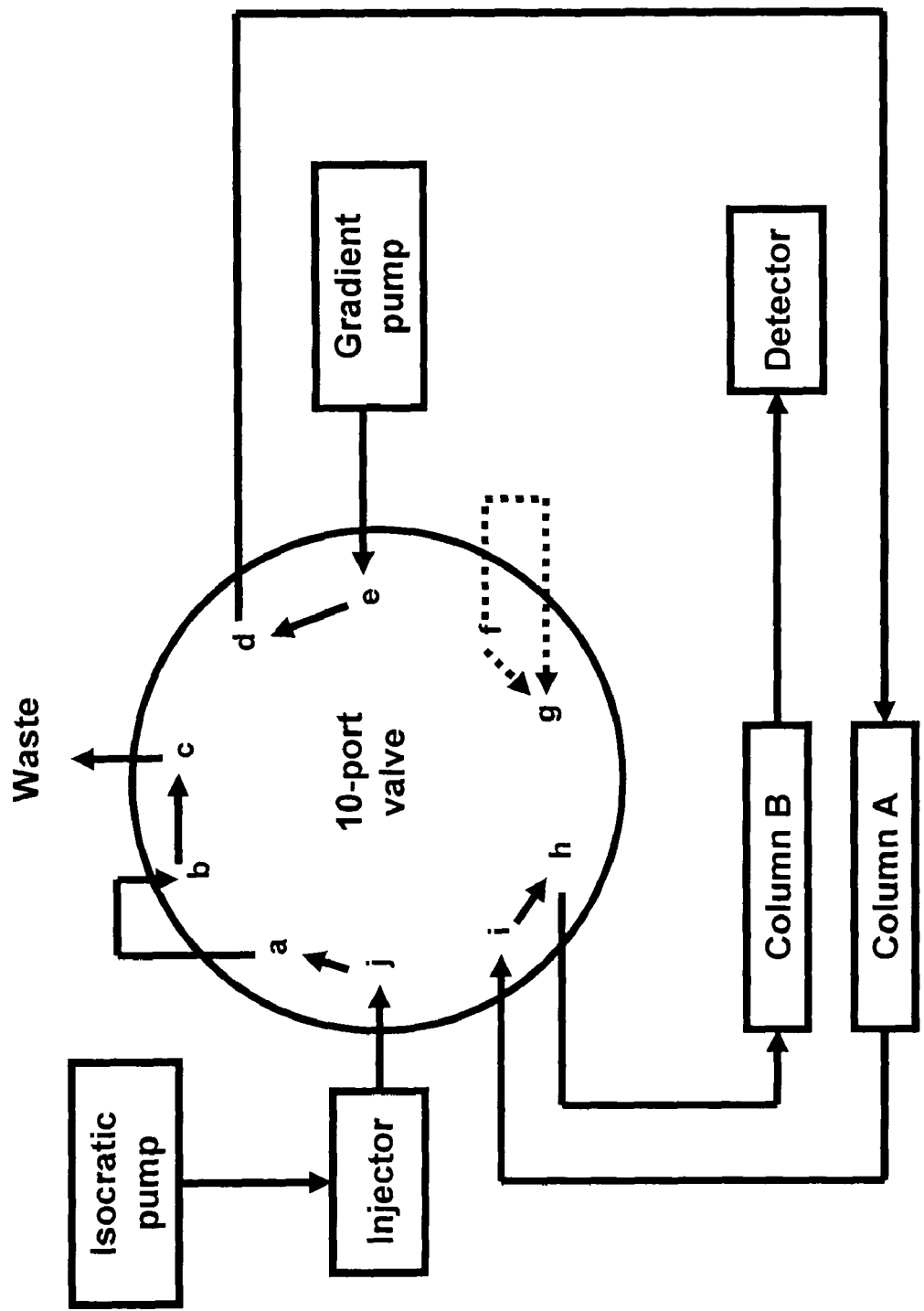
Figure 2A:
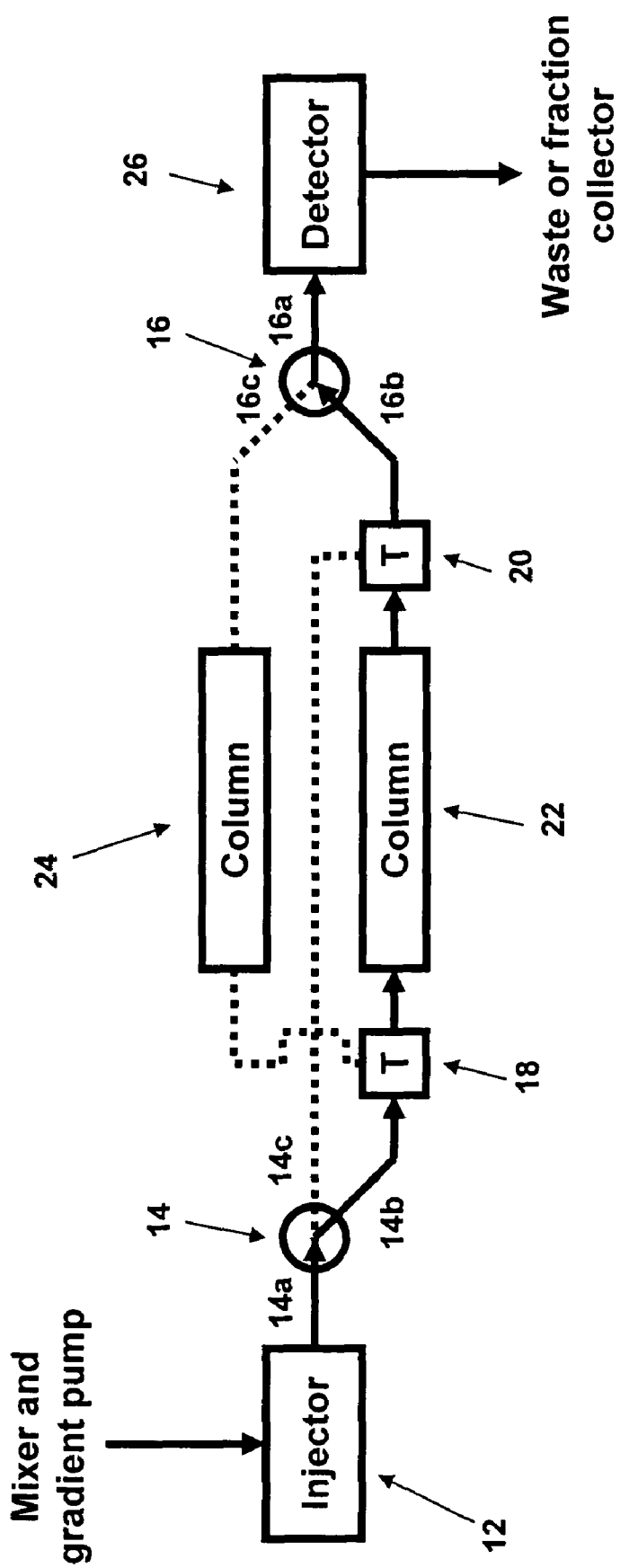
Figure 2B:
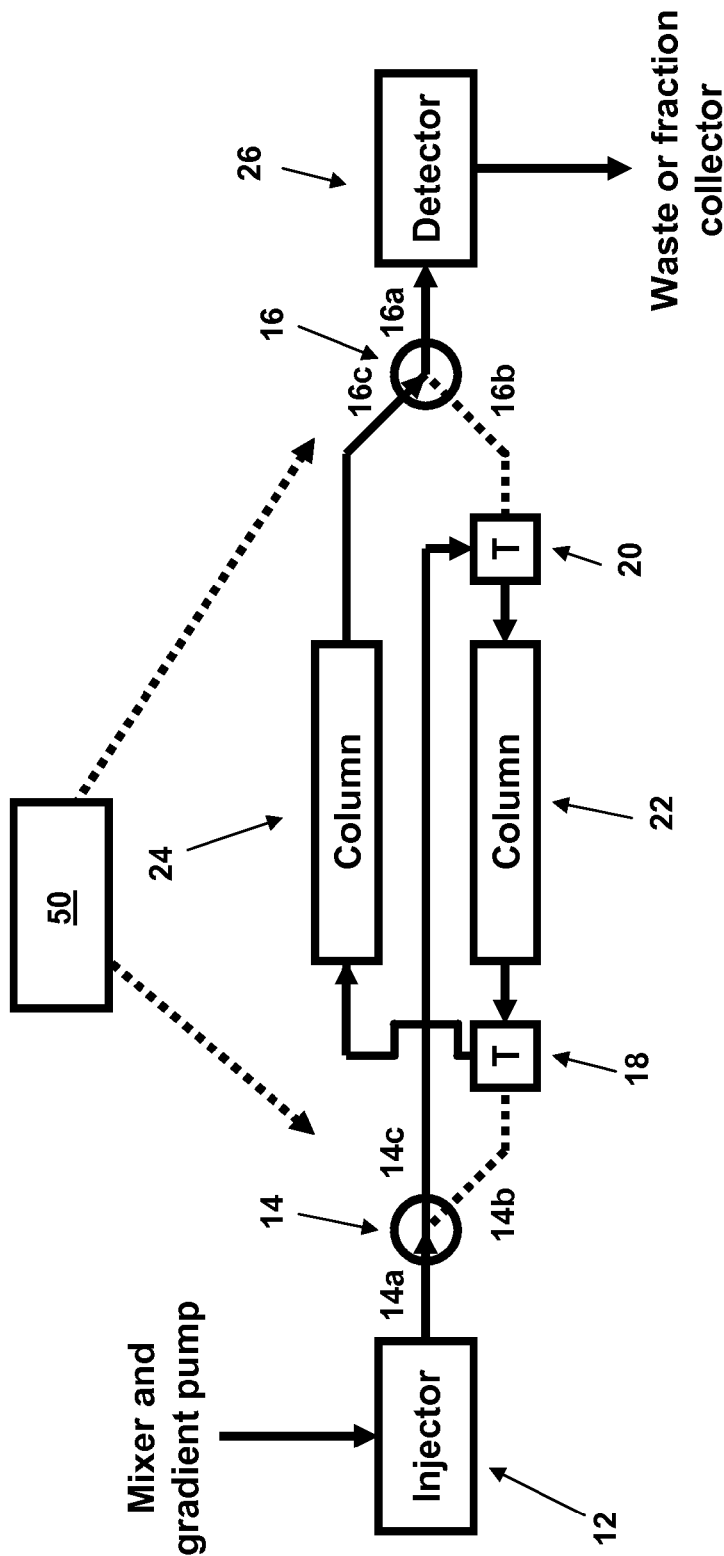

FIGS. 2a and 2b show the performance of the backflush process with an embodiment of the system according to the invention, wherein FIG. 2a presents the enrichment step and FIG. 2b presents the elution and separation step. First, a fluid, consisting, for example, of mobile phases from respective reservoirs, is supplied via a mixer and a gradient pump to an injector 12. For example, there may be four mobile phase reservoirs A, B, C and D. The injector 12 supplies the fluid to the first switch element 14, which, in this embodiment, has an input 14a and two mutually exclusive outputs 14b, 14c. In other words: when the first output 14b of the switch element is open, the second output 14c of the switch element is closed and vice versa. Such a function is provided, for example, by conventional two-way select valves. In the enrichment step presented in FIG. 2a, the first output 14b of the first switch element 14 is open and the second output 14c is closed, this position of the switch element providing a first, hereinbelow more fully described, fluidic path which is identified by arrows in the figures.

The first output 14b of the first switch element 14 is in fluidic communication with a first distributor element 18 with three ports, such as a T-connector, which, in turn, is in fluidic communication with a first separation column 22 at which the sample mixture contained in the fluid is enriched. As is known, a T-connector has three ports which may serve both as input and also as output. The first separation column 22, in turn, is in fluidic communication, via a second distributor element 20 with three ports, such as a T-connector, with a first input 16b of a second switch element 16. The second switch element 16 has two mutually exclusive inputs 16b, 16c as well as an output 16a. The output 16a of the second switch element 16 leads, for example, to a detector 26 and further to a fraction collector or to waste. As is indicated by the arrows in FIG. 2a, therefore, the fluidic path during the enrichment step runs from the injector 12 via the first switch element 14, the first distributor element 18, the first separation column 22, the second distributor element 20 and the second switch element 16 to the detector 26. The second separation column 24, which is in fluidic communication with the first distributor element 18 and the second input 16c of the second switch element 16, is decoupled from the fluid flow during enrichment (dotted fluid connections).

FIG. 2b presents the configuration of an embodiment of the system according to the invention during the second step of the backflush process, i.e. during elution of the first separation column 22 and during separation at the second separation column 24. In this case, the first output 14b of the first switch element 14 is closed and the second output 14c is open. The opening and closing of the mutually exclusive outputs is accomplished through the control means connected to the said elements, wherein said control means may be, for example, a suitably configured computer 50. The second output 14c of the first switch element 14 is in fluidic communication with the second distributor element 20. As is indicated by the arrows in FIG. 2b, therefore, the second fluidic path, i.e. the fluidic path for the elution and enrichment step, leads from the injector 12 via the first switch element 14 and the second distributor element 20 to the first separation column 22, wherein, in comparison with the flow direction for the enrichment step, the fluid flows in an opposite flow direction through the first separation column 22 to the first distributor element 18. The first distributor element 18 is further in fluidic communication with the second separation column 24, at which, for example, separation can take place, wherein said second separation column 24, in turn, is in fluidic communication with the second input 16c of the second switch element 16. Since, during the elution and enrichment step presented in FIG. 2b, the first input 16b of the second switch element 16 is now closed and the second input 16c is open, the second fluidic path runs from the first separation column 22 further via the first distributor element 18, the second separation column 24 to the second switching valve 16, as is indicated by the arrows. The output 16a of the second switching valve may be in fluidic communication, for example, with a detector 26 and/or with waste or with a fraction collector.

Consequently, by means of the above-described embodiment of the system according to the invention it is possible to enrich a separation mixture at the first separation column 22 (fluidic path 1) and, after switch elements 14, 16 have been switched over to fluidic path 2, the components of the separation mixture can be separated at separation column 24 using the backflush configuration, wherein, advantageously, it is not necessary to take into consideration any selectivity differences between the first and second separation columns 22, 24 and there is no peak widening. Surprisingly, it has further emerged that the performance of the backflush process by means of the above-described embodiment results in an improved sensitivity in comparison with the known arrangements.

Hereinbelow, further advantageous embodiments of the system according to the invention are described.

Figure 3A:
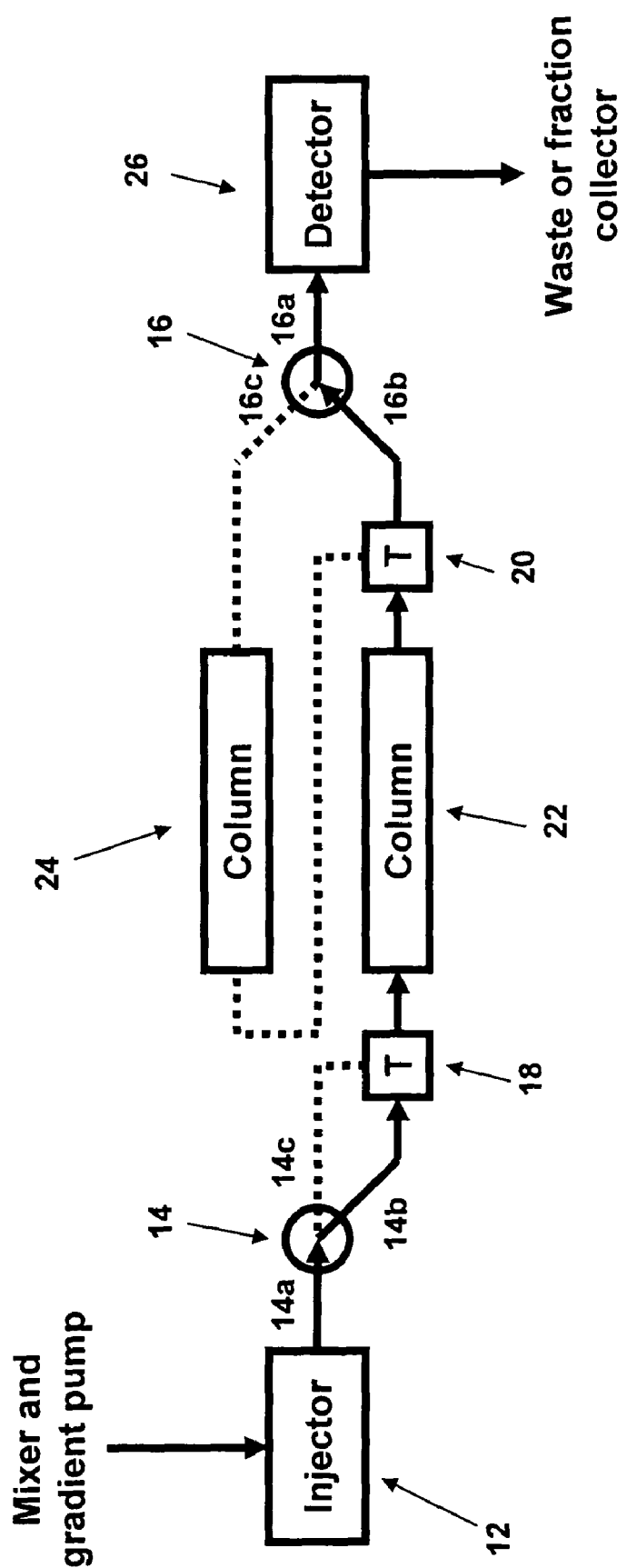
FIGS. 3a and 3b show a diagram of a further system according to the invention for sample preparation as well as two fluidic paths through the system, in which system a backflush process is not employed.
Figure 3B:
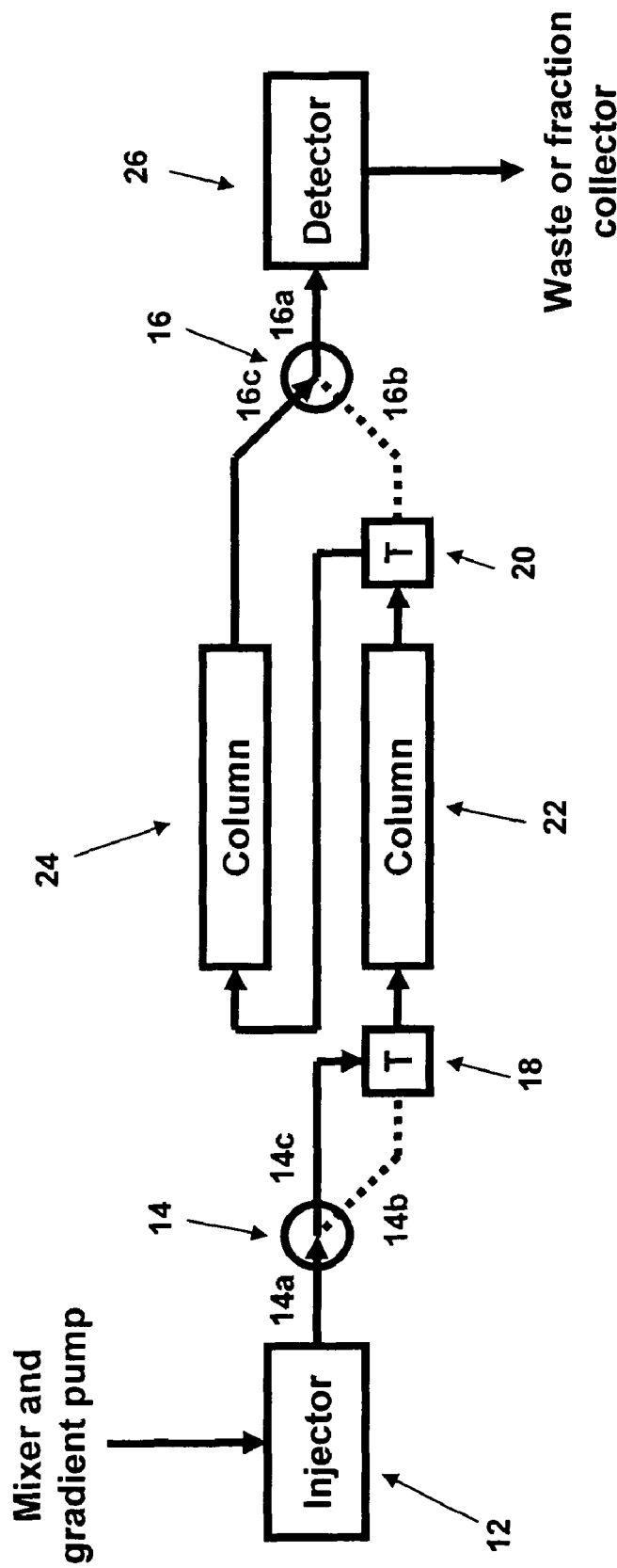

FIGS. 3a and 3b show a diagram of a further system according to the invention for sample preparation as well as two fluidic paths through the system, in which system a backflush process is not employed. The system components are the same as the system components of the embodiment presented in FIGS. 2a and 2b, but they are connected to each other slightly differently. The first fluidic path is the same as the above-described first fluidic path presented in FIGS. 2a and 2b. In contrast to the embodiment presented in FIGS. 2a and 2b, the second output 14c of the first switch element 14 is in fluidic communication with the first distributor element 18 and the second distributor element 20 is in fluidic communication with the second separation column 24. Consequently, the second fluidic path of the embodiment presented in FIGS. 3a and 3b (switch element output 14b and switch element input 16b closed and switch element output 14c and switch element input 16c open) leads from the injector 12 via the first switch element 14, the first distributor element 18, the first separation column 22, the second distributor element 20 and the second separation column 24 to the second switch element 16, as is indicated by the arrows in FIG. 3b. The output 16a of the second switch element 16 may be in fluidic communication, for example, with a detector 26 and/or with waste or with a fraction collector.

The possibilities which are offered by embodiments of the system according to the invention through the addition of a further fluidic path, and which are described hereinbelow, include, for example, embodiments for fast flushing, 2D chromatography, the use of another or further separation columns and column selection. The switch elements 14, 16 used in the below-described embodiments have, respectively, an input 14a and three mutually exclusive outputs 14b, 14c, 14d and an output 16 and three mutually exclusive inputs 16b, 16c, 16d.

Figure 4A:
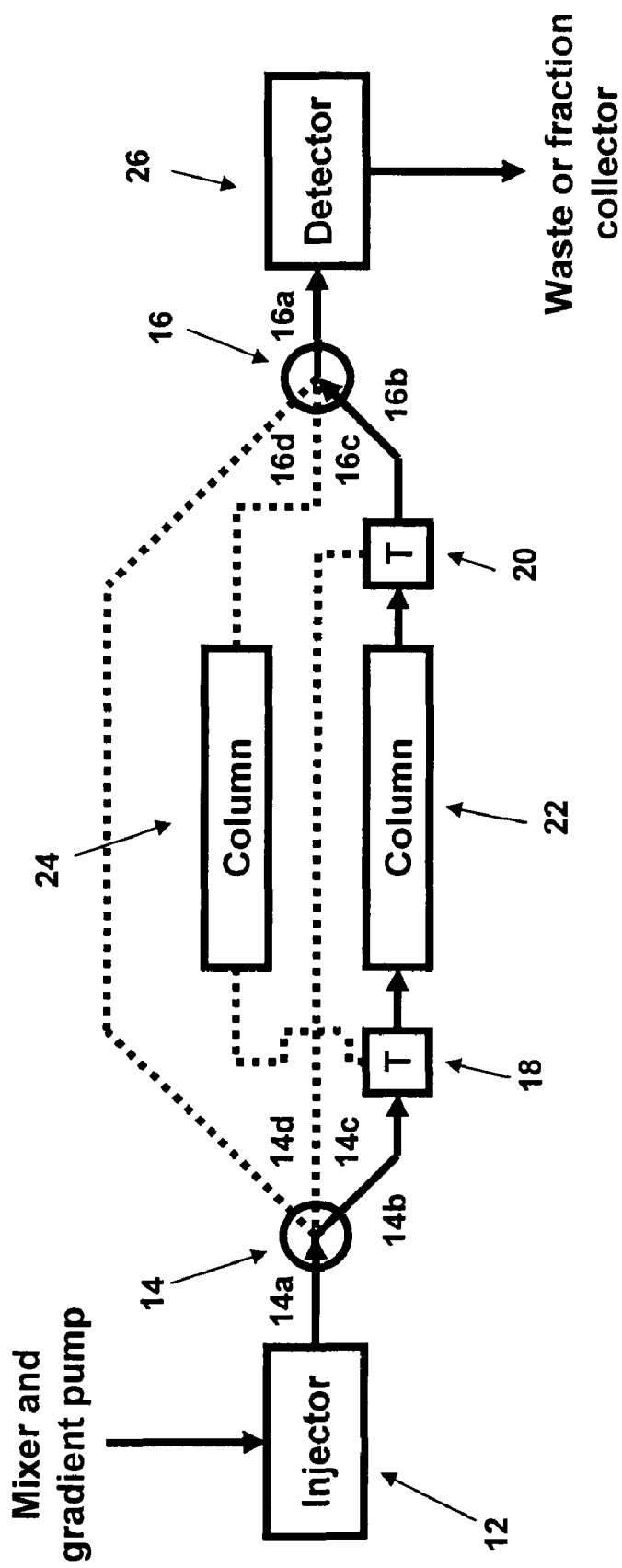
FIGS. 4a, 4b and 4c show a diagram of a further system according to the invention for sample preparation as well as three fluidic paths through the system, said system allowing fast flushing.
Figure 4B:
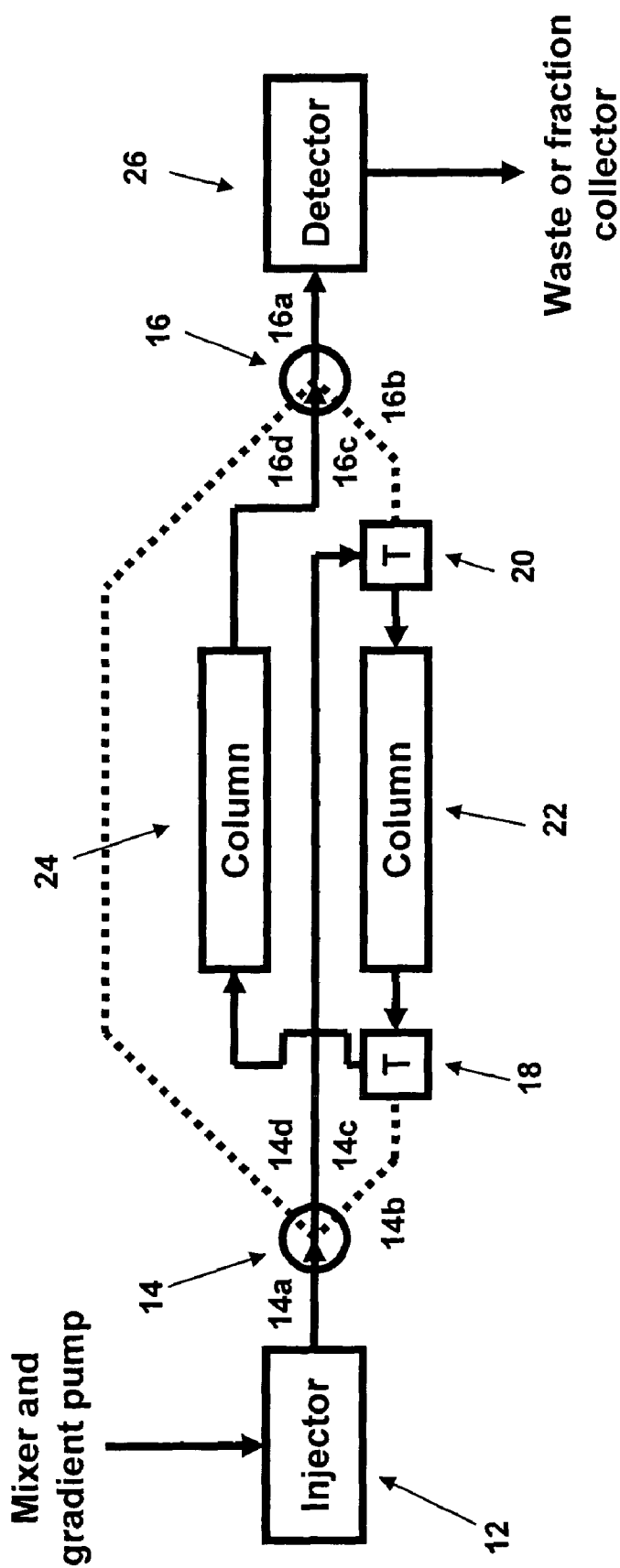
Figure 4C:
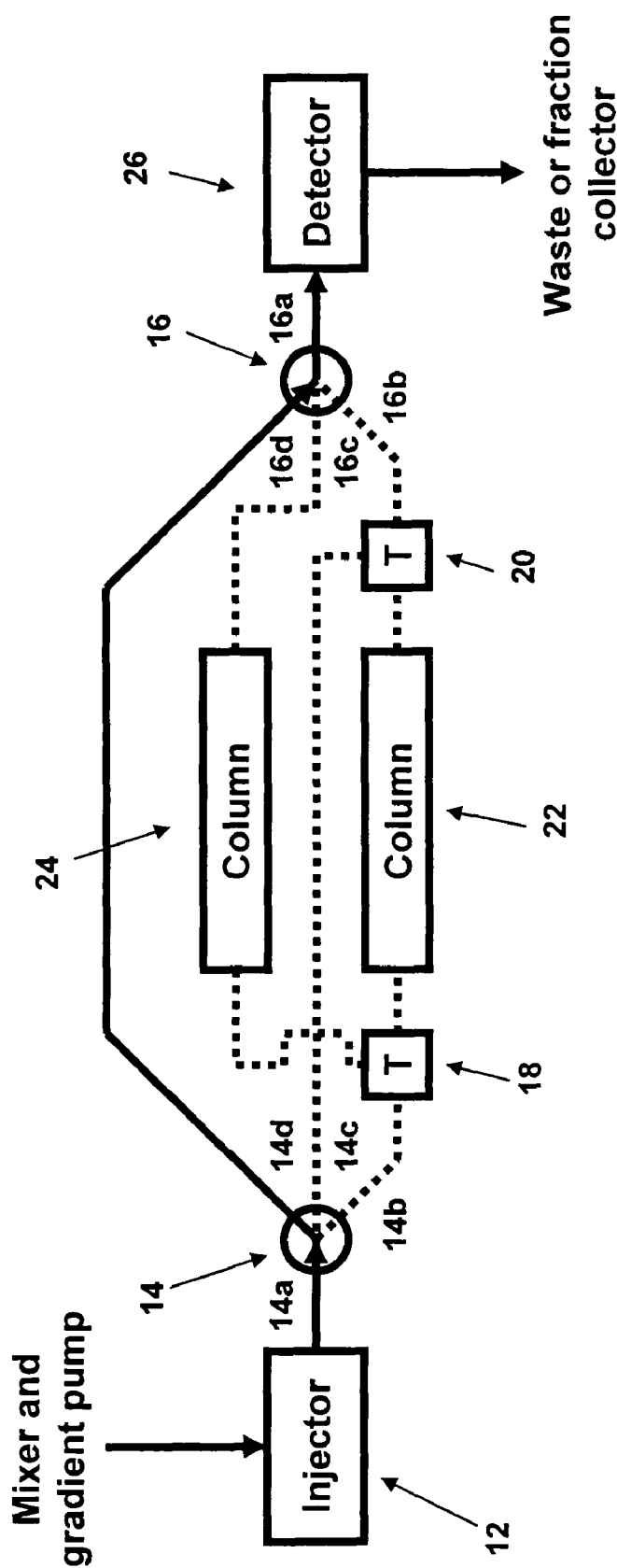

The embodiment of the system according to the invention presented in FIGS. 4a, 4b and 4c differs from the embodiment presented in FIGS. 2a and 2b in that the third switch element output 14d of the first switch element is in fluidic communication with the third switch element input 16d of the second switch element 16. This configuration permits fast flushing, for example, of the detector 26, because the third fluidic path runs directly from the injector via the first switch element 14 and the second switch element 16 to the detector 26.

Figure 5:
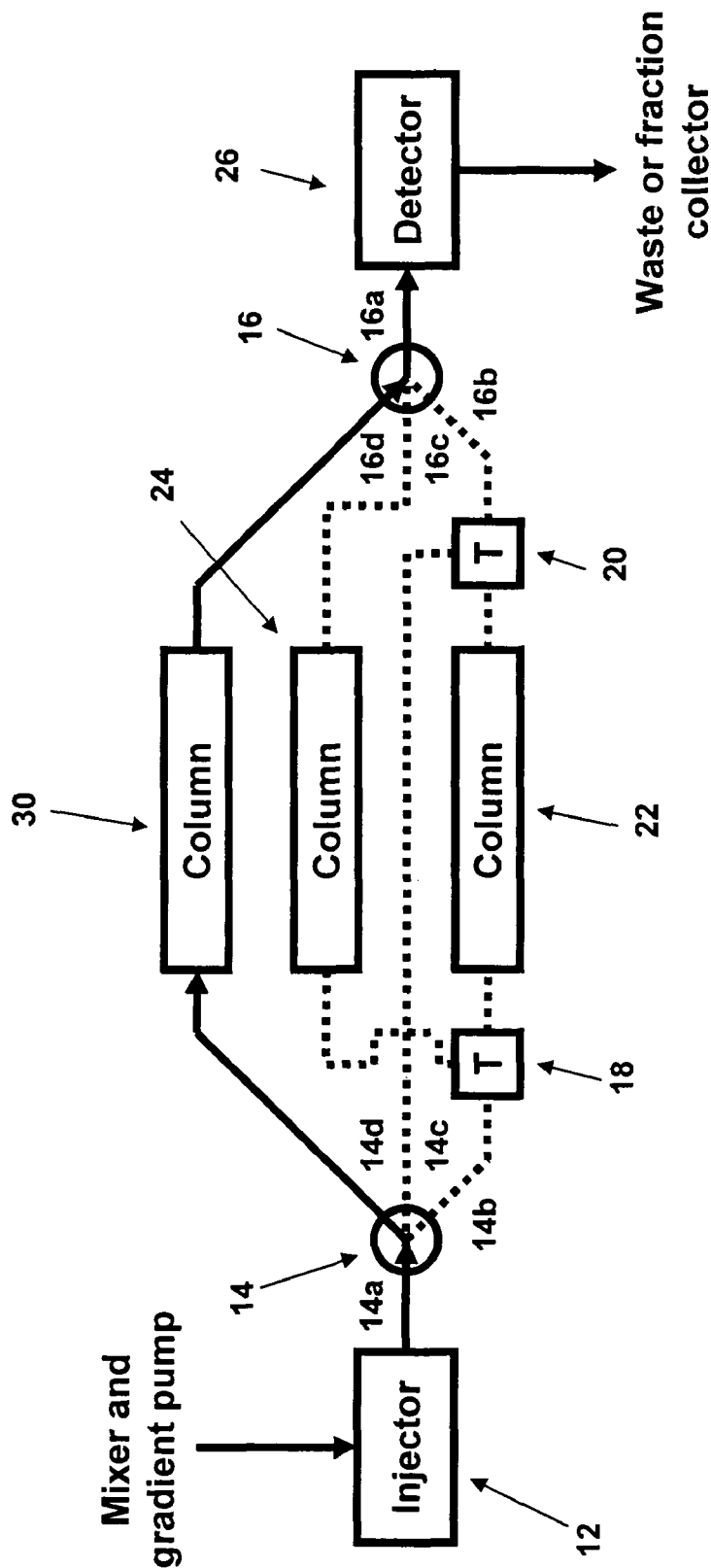
FIG. 5 shows a diagram of a further system according to the invention for sample preparation as well as one fluidic path, said system allowing the use of a further separation column.

The embodiment of the system according to the invention presented in FIG. 5 is the same as the embodiment presented in FIGS. 4a, 4b and 4c, but, in this case, there is a third separation column 30 in the third fluidic path between the third switch element output 14d of the first switch element 14 and the third switch element input 16d of the second switch element 16. In addition to the possibilities provided by the above-described embodiment of the invention presented in FIGS. 2*a* and 2*b*, such an embodiment allows sample separation by means of separation column 30 without sample preparation.

Figure 6A:
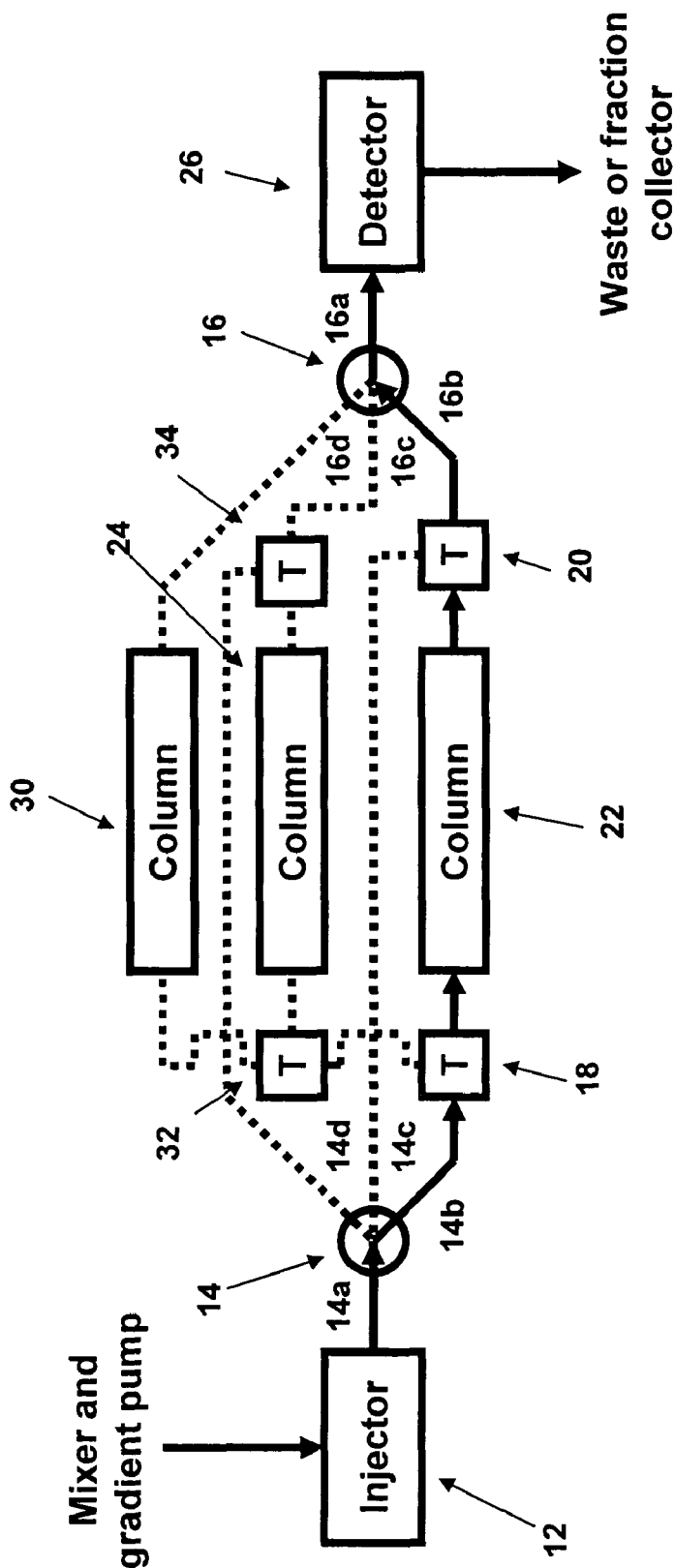
FIGS. 6a, 6b and 6c show a diagram of a further system according to the invention for sample preparation as well as three fluidic paths through the system, said system allowing two-dimensional chromatography.
Figure 6B:
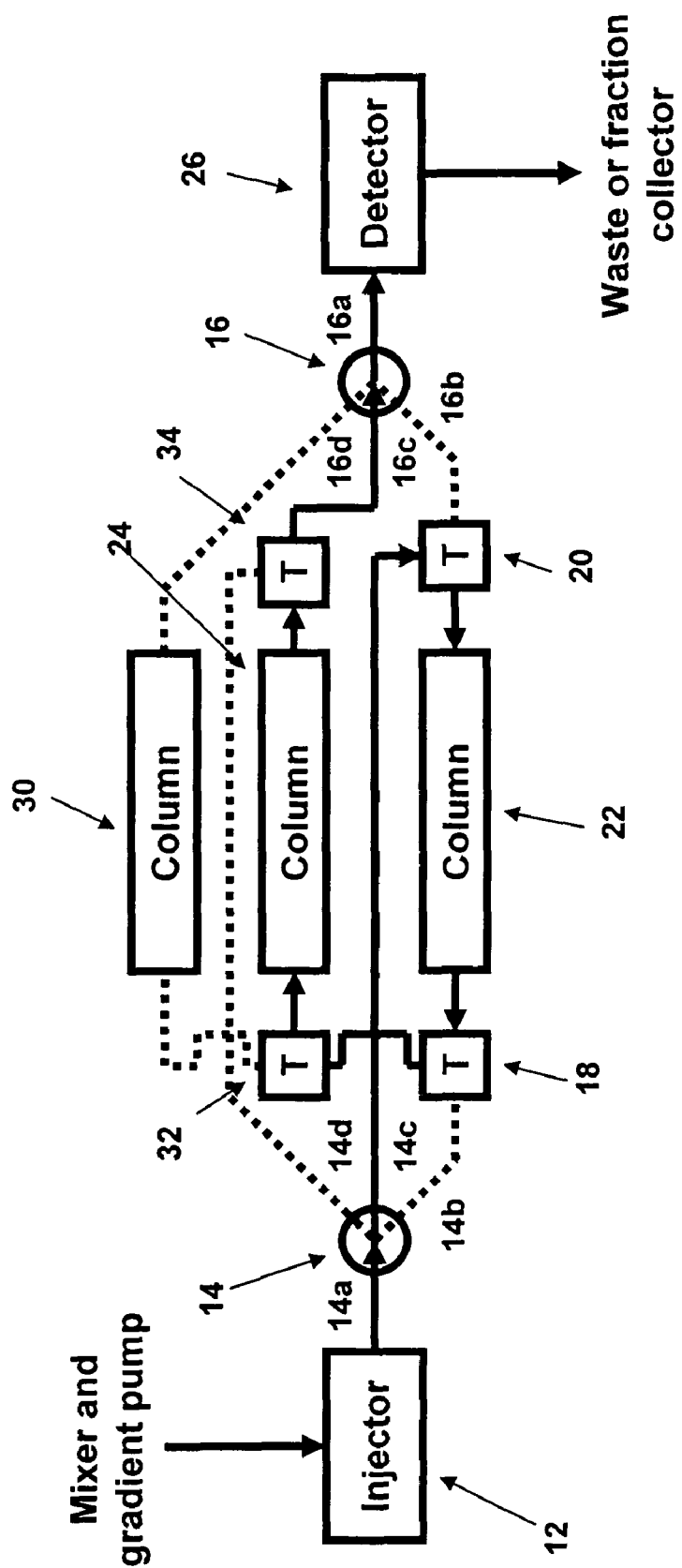
Figure 6C:
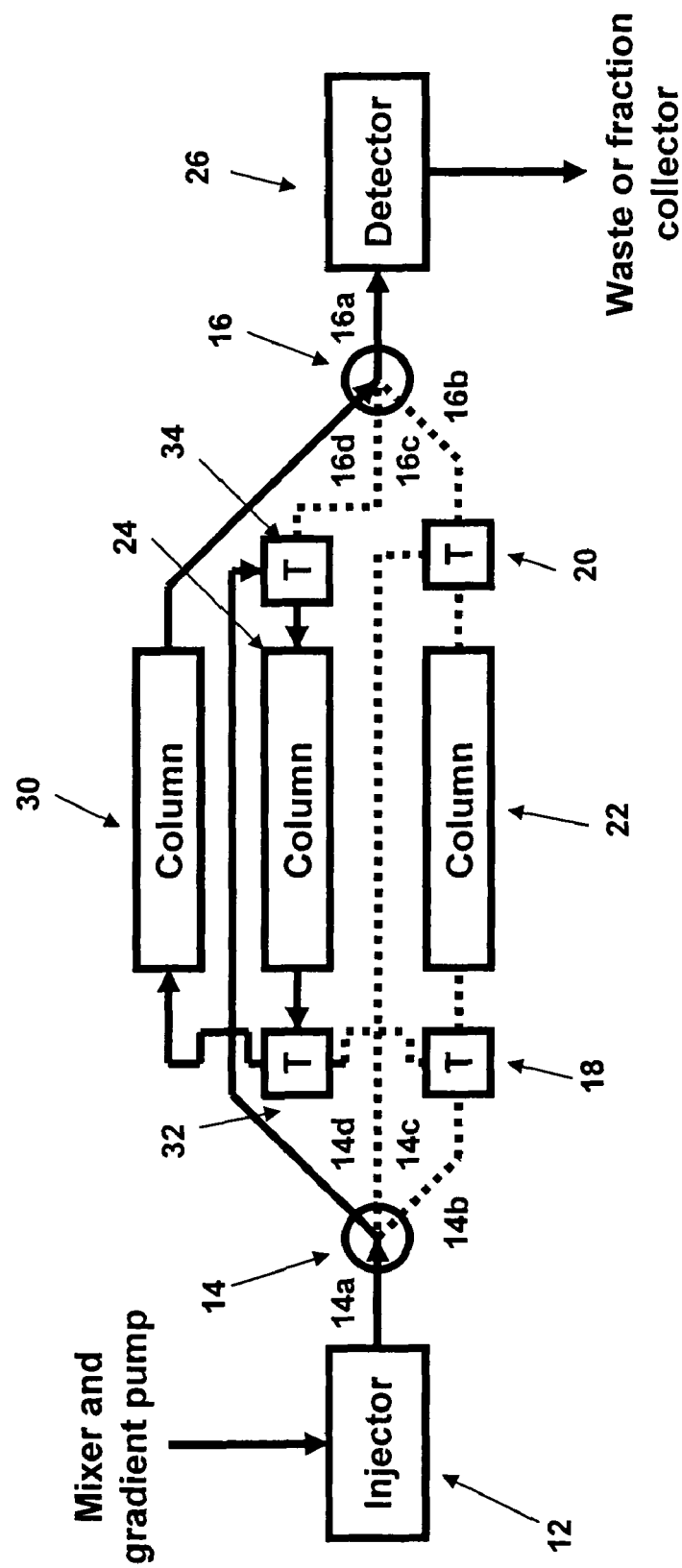

The embodiment of the system according to the invention presented in FIGS. 6*a*, 6*b* and 6*c* has, in addition to the embodiment presented in FIGS. 2*a* and 2*b*, an additional separation column 30 as well as a third distributor element 32 with three ports, such as a T-connector, and a fourth distributor element 34 with three ports, such as a T-connector. These are connected to the remaining components of the above-described embodiments such that the first and second fluidic paths are the same as the first and second fluidic paths of the above-described embodiment presented in FIGS. 2*a* and 2*b*, as is indicated by the arrows in FIGS. 6*a* and 6*b*, wherein the second fluidic path additionally leads through the third and fourth distributor elements 32, 34, which are in fluidic communication with the second separation column 24. The additional third fluidic path runs from the third output 14*d* of the first switch element 14 via the fourth distributor element 34, the second separation column 24, the third distributor element and the third separation column 30 to the third input 16*d* of the second switch element 16, the fluid flowing through the second separation column 24 in a direction opposite to the flow direction of the second fluidic path through the second separation column 24. The output 16*a* of the second switch element 16 may be in fluidic communication, for example, with a detector 26 and/or with waste or with a fraction collector.

Figure 7A:
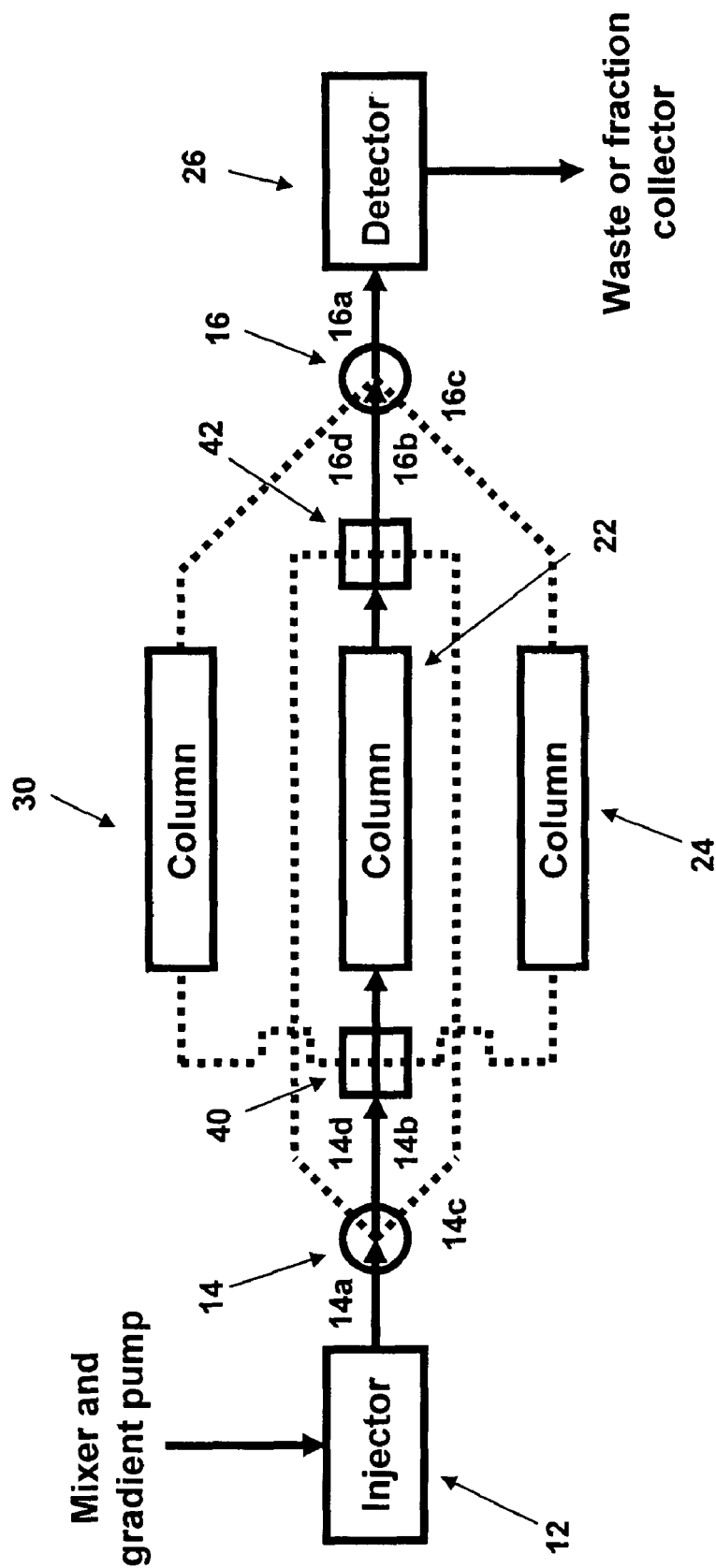
FIGS. 7a, 7b and 7c show a diagram of a further system according to the invention for sample preparation as well as three fluidic paths through the system, said system allowing selection from between two separation columns.
Figure 7B:
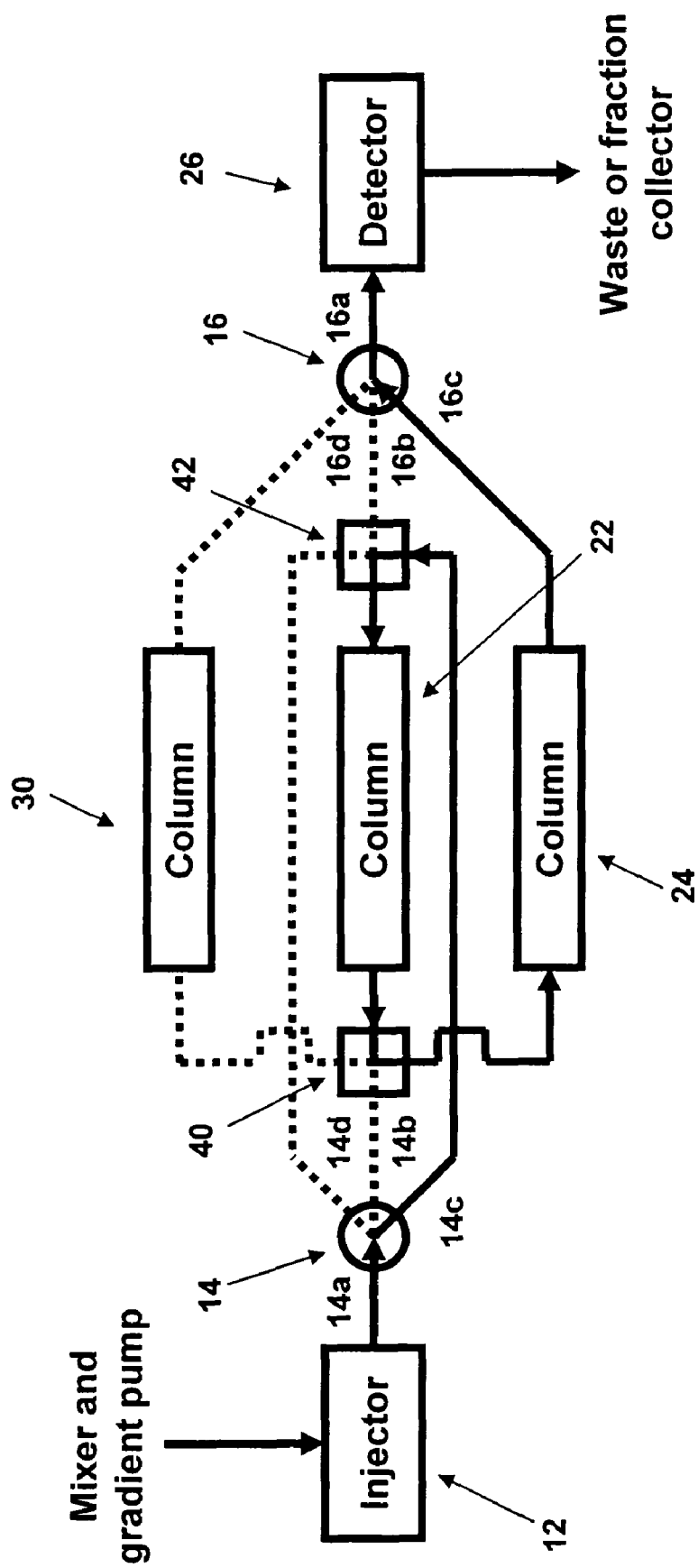
Figure 7C:
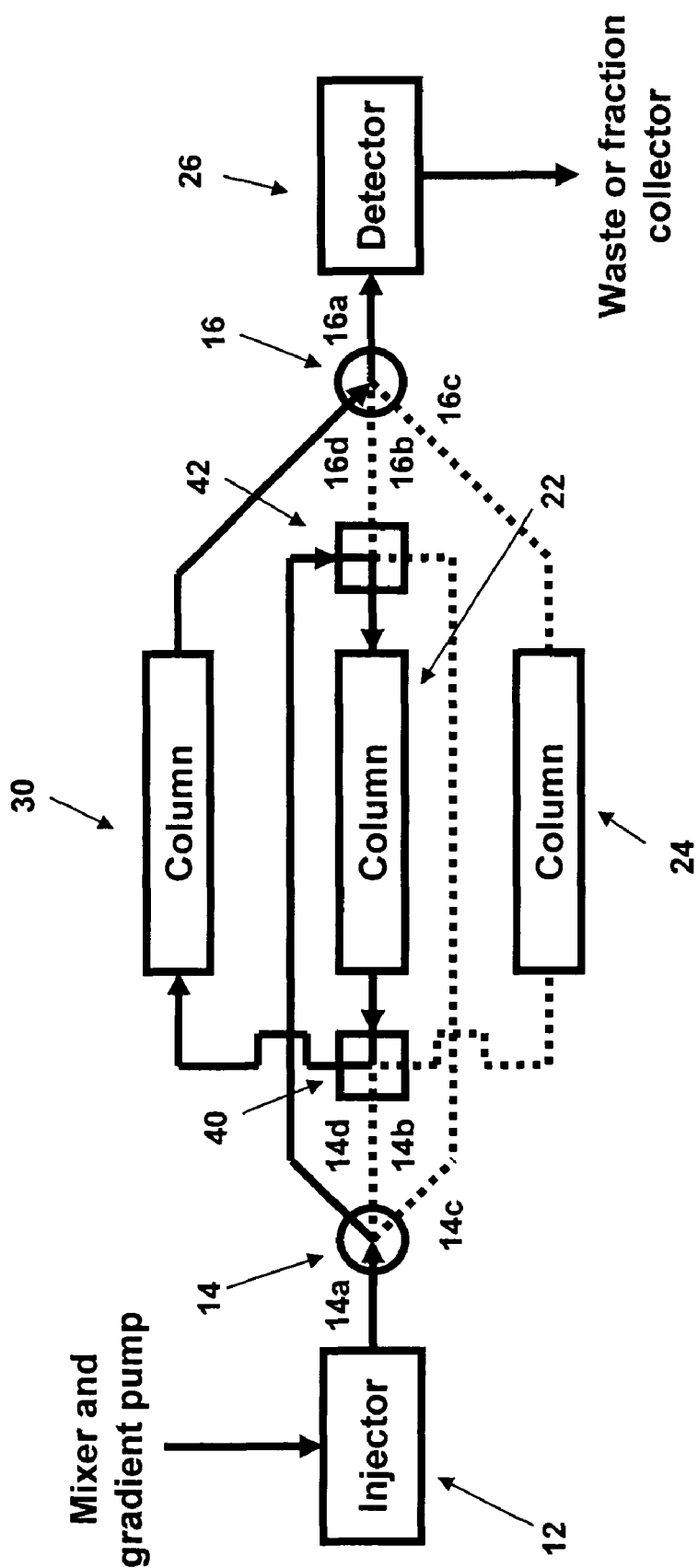

The embodiment of the system according to the invention presented in FIGS. 7*a*, 7*b* and 7*c* comprises, instead of the 3-port distributor elements employed in the above-described embodiments, a first distributor element 40 with four ports, such as a cross-connector, and a second distributor element 42 with four ports, such as a cross-connector, in addition to the components described in the above embodiments. As is known, a cross-connector has four ports which can serve both as input and also as output. The first distributor element 40 is in fluidic communication with the first output 14*b* of the switch element 14, the first separation column 22, the second separation column 24 and the third separation column 30. The second distributor element 42 is in fluidic communication with the first separation column 22, the second output 14*c* and the third output 14*d* of the first switch element 14 and the first input 16*b* of the second switch element 16. Furthermore, the second input 16*c* of the second switch element 16 is in fluidic communication with the second separation column 24, and the third input 16*d* of the second switch element 16 is in fluidic communication with the third separation column 30. Consequently, the arrangement and connection of the components presented in FIGS. 7*a*, 7*b* and 7*c* makes it possible, in addition to the possibilities provided by the above-described embodiments presented in FIGS. 2*a* and 2*b*, for separation to be performed, depending on the user's preferences, at the second or third separation column 24, 30. Enrichment of the sample takes place, as in the embodiment presented in FIGS. 2*a* and 2*b*, at the first separation column 22.

With reference to the above-described embodiments, the person skilled in the art will realize that, on the basis of the system according to the invention, it is possible to implement further advantageous configurations which can advantageously be used in sample preparation, sample enrichment, preparatory chromatography and the like. Common to all these configurations is the fact that the combination of switch elements, distributor elements and separation columns as employed in the system according to the invention makes it possible, depending on the user's needs, to provide different fluidic paths through the system by means of which the above-described advantageous processes can be performed.

What is claimed is:

1. System for sample preparation and/or sample enrichment, the system comprising the following components:
   a gradient pump for supplying fluid to an injector (12);
   a first switch element (14) with a switch element input (14*a*) and at least two mutually exclusive switch element outputs (14*b*, 14*c*, 14*d*) and a second corresponding switch element (16) with at least two mutually exclusive switch element inputs (16*b*, 16*c*, 16*d*) and a switch element output (16*a*), the first and second switch elements being connected to control means for opening and closing the switch element inputs (14*a*, 16*b*, 16*c*, 16*d*) and switch element outputs (14*b*, 14*c*, 14*d*, 16*a*);
   a first distributor element (18, 40) with at least three ports and a second distributor element (20, 40) with at least three ports; as well as
   a first separation column (22) and a second separation column (24),
   wherein the components are arranged in such fluidic communication with each other that by means of different positions of the switch elements (14, 16), achievable through the control means, it is possible to configure at least two different fluidic paths in the system, such that
   in sequence, the injector (12), the first switch element (14), the first distributor element (18), the first separation column (22), the second distributor element (20) and the second switch element (16) are in such fluidic communication that they configure a first fluidic path when the switch elements (14, 16) are in a first position, and
   in sequence, the injector (12), the first switch element (14), the second distributor element (20), the first separation column (22), the first distributor element (18), the second separation column (24) and the second switch element (16) are in such fluidic communication that they configure a second fluidic path when the switch elements (14, 16) are in a second position, with the result that
   the flow direction along the first fluidic path through the first separation column (22) is opposite to the flow direction of the second fluidic path through said first separation column (22).

2. System for sample preparation, comprising:
   a first switch element (14) with a switch element input (14*a*) and at least two mutually exclusive switch element outputs (14*b*, 14*c*, 14*d*) and a second corresponding switch element (16) with at least two mutually exclusive switch element inputs (16*b*, 16*c*, 16*d*) and a switch element output (16*a*), the first and second switch elements being connected to control means for opening and closing the switch element inputs (14*a*, 16*b*, 16*c*, 16*d*) and switch element outputs (14*b*, 14*c*, 14*d*, 16*a*);
   a first distributor element (18, 40) with at least three ports and a second distributor element (20, 40) with at least three ports; as well as
   a first separation column (22) and a second separation column (24),
   the components being in such fluidic communication with each other that, through different positions of the switch elements (14, 16), said different positions being achievable through the control means, it is possible to configure at least two different fluidic paths in the system,
   wherein the first switch element (14) has three mutually exclusive outputs (14*b*, 14*c*, 14*d*) and the second corresponding switch element (16) has three mutually exclusive inputs (16*b*, 16*c*, 16*d*), wherein the third output (14d) of the first switch element (14) is in direct fluidic communication with the third input (16c) of the second switch element (16).

3. System for sample preparation, comprising:
a first switch element (14) with a switch element input (14a) and at least two mutually exclusive switch element outputs (14b, 14c, 14d) and a second corresponding switch element (16) with at least two mutually exclusive switch element inputs (16b, 16c, 16d) and a switch element output (16a), the first and second switch elements being connected to control means for opening and closing the switch element inputs (14a, 16b, 16c, 16d) and switch element outputs (14b, 14c, 14d, 16a);
a first distributor element (18, 40) with at least three ports and a second distributor element (20, 40) with at least three ports; as well as
a first separation column (22) and a second separation column (24),
the components being in such fluidic communication with each other that, through different positions of the switch elements (14, 16), said different positions being achievable through the control means, it is possible to configure at least two different fluidic paths in the system,
wherein the first switch element (14) has three mutually exclusive outputs (14b, 14c, 14d) and the second corresponding switch element (16) has three mutually exclusive inputs (16b, 16c, 16d), wherein the third output (14d) of the first switch element (14) is in fluidic communication with a third separation column (30), said third separation column (30), in turn, being in fluidic communication with the third input (16c) of the second switch element (16).

4. System according to claim 1, wherein the system further comprises a third distributor element (32) with three ports, a fourth distributor element (34) with three ports and a third separation column (30), wherein the first switch element (14) has three mutually exclusive outputs (14b, 14c, 14d) and the second corresponding switch element (16) has three mutually exclusive inputs (16b, 16c, 16d), wherein, in sequence, the switch element (14), the first distributor element (18), the first separation column (22), the second distributor element (20) and the second switch element (16) are in such fluidic communication that they configure a first fluidic path when the switch elements (14, 16) are in a first position, wherein, in sequence, the switch element (14), the second distributor element (20), the first separation column (22), the first distributor element (18), the third distributor element (32), the second separation column (24), the fourth distributor element (34) and the second switch element (16) are in such fluidic communication that they configure a second fluidic path when the switch elements (14, 16) are in a second position, and wherein, in sequence, the first switch element (14), the fourth distributor element (34), the second separation column (24), the third distributor element (32), the third separation column (30) and the second switch element (16) are in such fluidic communication that they configure a third fluidic path when the switch elements (14, 16) are in a third position.

5. System according to claim 1, wherein the first distributor element (40) and the second distributor element each have four ports and the system further comprises a third separation column, wherein, in sequence, the first switch element (14), the first distributor element (40), the first separation column (22), the second distributor element (42) and the second switch element (16) are in such fluidic communication that they configure a first fluidic path when the switch elements (14, 16) are in a first position, wherein, in sequence, the first switch element (14), the second distributor element (42), the first separation column (22), the first distributor element (40), the second separation column (24) and the second switch element (16) are in such fluidic communication that they configure a second fluidic path when the switch elements (14, 16) are in a second position, and wherein, in sequence, the first switch element (14), the second distributor element (42), the first separation column (22), the first distributor element (40), the third separation column (30) and the second switch element (16) are in such fluidic communication that they configure a third fluidic path when the switch elements (14, 16) are in a third position.

6. System according to any one of claims 1 to 5, wherein the system further has a detector (26).

7. System according to any one of claims 1 to 5, wherein the switch elements (14, 16) are path selection valves.

8. System according to any one of claims 1 to 4, wherein the distributor elements (18, 20, 32, 34) are T-connectors.

9. System according to claim 5, wherein the distributor elements (40, 42) are cross-connectors.

10. Method for sample preparation by means of the back-flush process, wherein the method comprises the following steps:
provision of a system according to claim 1 when the switch elements (14, 16) are in the first position;
conveying of a fluid along the first fluidic path;
switching of the switch elements (14, 16) into the second position of the switch elements (14, 16) and
conveying of a fluid along the second fluidic path such that the flow direction along the first fluidic path through the first separation column is opposite to the flow direction of the second fluidic path through said first separation column.

* * * * *